(12) United States Patent
Rheiner et al.

(10) Patent No.: US 11,812,982 B2
(45) Date of Patent: Nov. 14, 2023

(54) EARS, NOSE, AND THROAT EXTRACTOR

(71) Applicant: Veartech, Inc., Seguin, TX (US)

(72) Inventors: John Rheiner, New Braunfels, TX (US); Terry Young, La Vernia, TX (US)

(73) Assignee: Veartech, Inc., Seguin, TX (US)

( * ) Notice: Subject to any disclaimer, the term of this patent is extended or adjusted under 35 U.S.C. 154(b) by 364 days.

(21) Appl. No.: 17/315,098

(22) Filed: May 7, 2021

(65) Prior Publication Data

US 2021/0346043 A1 Nov. 11, 2021

Related U.S. Application Data

(60) Provisional application No. 63/021,807, filed on May 8, 2020.

(51) Int. Cl.
*A61B 17/00* (2006.01)
*A61B 17/24* (2006.01)
*A61B 17/22* (2006.01)

(52) U.S. Cl.
CPC .............. *A61B 17/24* (2013.01); *A61B 17/22* (2013.01); *A61B 2017/00367* (2013.01); *A61B 2017/00477* (2013.01); *A61B 2017/00544* (2013.01); *A61B 2017/00787* (2013.01); *A61B 2017/246* (2013.01); *A61B 2217/005* (2013.01)

(58) Field of Classification Search
CPC .... A61B 2017/22079; A61B 2017/246; A61B 2017/306; A61B 2217/005; A61B 2017/00787; A61B 17/24
See application file for complete search history.

*Primary Examiner* — Deanna K Hall
(74) *Attorney, Agent, or Firm* — Patent Capital Group

(57) ABSTRACT

There is disclosed in one example an apparatus for extracting a foreign body (FB) from a bodily orifice, including: a connector having a receiver to pneumatically seal to a suction source; a hollow shaft pneumatically coupled to the connector; a hollow tip pneumatically coupled to the hollow shaft; and a valve disposed between the hollow tip and the connector, wherein the valve is biased to an open position, and the valve, when closed pneumatically isolates the hollow tip from the connector, and when open allows a continuous air flow passage between the connector and the hollow tip; and means to release the valve, whereby the valve opens when the means are activated.

40 Claims, 6 Drawing Sheets

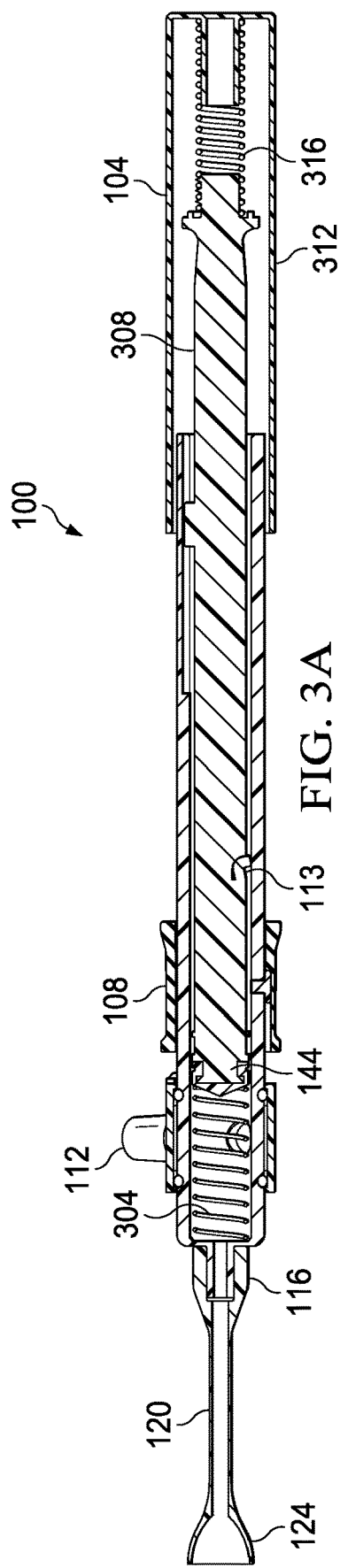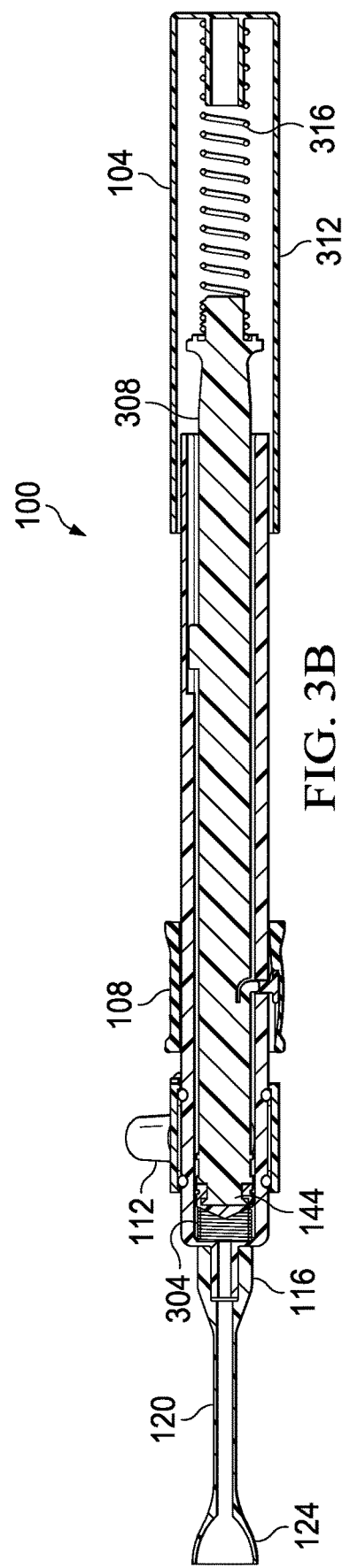

EARS, NOSE, AND THROAT EXTRACTOR

FIELD OF THE SPECIFICATION

This application relates in general to medical foreign body extraction, and more particularly, though not exclusively, to a system and method of providing an extractor for the ears, nose, and throat.

BACKGROUND

Foreign bodies that become lodged in the ears, nose, and throat, whether by insertion, swallowing, aspiration, or by other means, can cause a variety of complications. These may include suffocation risk, difficulty hearing or breathing, as well as the danger of infection. Safe, effective removal of foreign bodies is a common requirement in the clinical office environment.

BRIEF DESCRIPTION OF THE DRAWINGS

The present disclosure is best understood from the following detailed description when read with the accompanying FIGURES. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion. Furthermore, the various block diagrams illustrated herein disclose only one illustrative arrangement of logical elements. Those elements may be rearranged in different configurations, and elements shown in one block may, in appropriate circumstances, be moved to a different block or configuration.

FIGS. 3A and 3B are a cutaway side view of an ENT extractor assembly.

SUMMARY

Figure 1A:
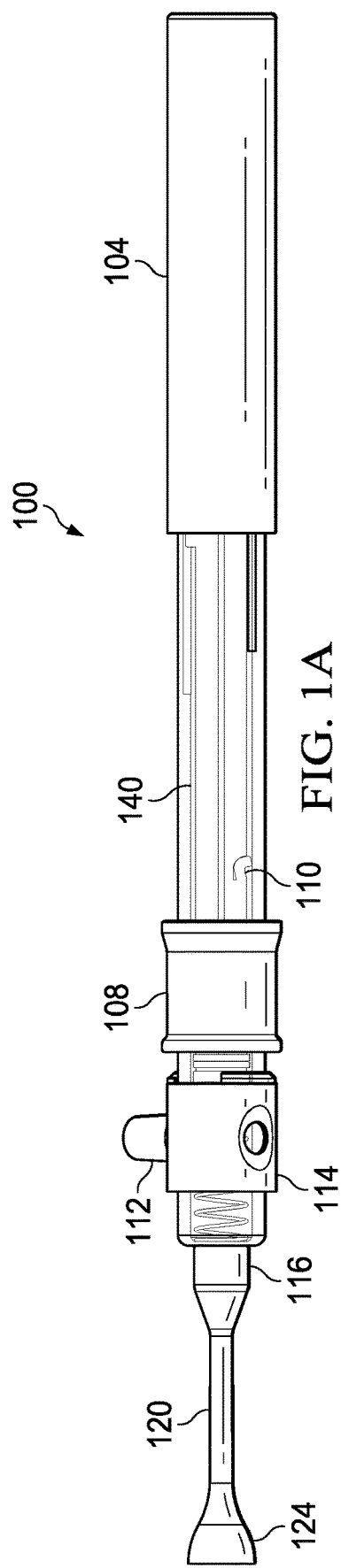
FIGS. 1A and 1B illustrate selected elements of a side view of an ears, nose, and throat (ENT) extractor.

In an example, there is disclosed an apparatus for extracting a foreign body (FB) from a bodily orifice, comprising: a connector having a receiver to pneumatically seal to a suction source; a hollow shaft pneumatically coupled to the connector; a hollow tip pneumatically coupled to the hollow shaft; and a valve disposed between the hollow tip and the connector, wherein the valve is biased to an open position, and the valve, when closed pneumatically isolates the hollow tip from the connector, and when open allows a continuous air flow passage between the connector and the hollow tip; and means to release the valve, whereby the valve opens when the means are activated.

Embodiments of the Disclosure

The following disclosure provides many different embodiments, or examples, for implementing different features of the present disclosure. Specific examples of components and arrangements are described below to simplify the present disclosure. These are, of course, merely examples and are not intended to be limiting. Further, the present disclosure may repeat reference numerals and/or letters in the various examples. This repetition is for the purpose of simplicity and clarity and does not in itself dictate a relationship between the various embodiments and/or configurations discussed. Different embodiments may have different advantages, and no particular advantage is necessarily required of any embodiment.

Young children, many at toddler age, commonly put small objects or foreign bodies (FBs) in the nose, mouth, or ears. These FBs may be organic matter (such as beans, peas, or other foods), stones, or hard plastic, and are often smooth with few or no edges. Removing them from the ear or nose of a child—usually struggling and/or crying—is a challenge. In existing practice, an instrument may be used to remove the object, such as one with a pointed tip, such as forceps or hemostats. Grasping an FB with such instruments may be difficult, and may require a skilled ENT physician, physician's assistant, or nurse. The present specification discloses an apparatus and method for use that provides a simplified and safety-enhanced mechanism for removing FBs. The instrument may be inexpensive, or may include inexpensive disposable parts, and may be simple to use. Advantageously, this enables an ENT practitioner or other medical professional to use the device more efficiently and effectively. Furthermore, embodiments of the device may be simple enough for home use, which may eliminate the need for a visit to an ENT professional. Advantageously, embodiments of the present disclosure may also be used to remove other FBs, including cerumen from the ear canal.

In an embodiment, an extractor includes two parts. The first part is a reusable handheld device, which in an illustrative embodiment is approximately the size of a pen. This may provide various means for developing a vacuum or suction action, such as a spring-loaded plunger to create a rapid transient suction, or a plunger that can be drawn back to prime the vacuum, and a spring-loaded valve that releases the vacuum, thus creating a rapid transient suction. The second part is a disposable and removable tip designed with a variety of spray patterns that can be used with other suction devices. A disposable tip can be affixed to the handheld suction device, which is used to remove foreign bodies from an orifice (e.g., the nose, by way of nonlimiting example). The device is designed to allow a user to apply suction either from micro-suction via the device, or continuous suction from an outside source to "pull" a smooth FB to the tip. In some embodiments, the suction itself is sufficient to hold the FB. To provide further securing strength, the illustrated tip may be treated with a highly sticky or tacky materials, which can help to secure the FB in place while it is removed from the orifice.

Advantageously, the device is capable of generating its own suction. This is accomplished, in one embodiment, with a plunger or piston that pneumatically seals to a barrel, and is used to prime the vacuum, and a spring-loaded valve attached to a trigger that releases the vacuum, and creates suction. In another embodiment, suction is accomplished by way of a spring-loaded internal plunger that rapidly actuates when the user depresses a button, thus releasing the spring. In yet another embodiment, an attachment may be provided for an off-the-shelf syringe, such as a 10 mL oral syringe or other, wherein the syringe provides the piston and barrel, and the attachment provides a valve. The piston of the syringe can be pulled back to develop a vacuum, and the valve may then be released to create suction.

In some embodiments, the device may also be connected to an external continuous suction pump via a collared port that, on one side, has a nipple for connecting to the hose. On the opposite side of the collar, there is an opening that may be controlled by the user to regulate the amount of suction applied when using continuous suction via the external suction pump. To use the device for continuous suction, the user may rotate the collar to align with two holes on the device, which allow the flow of suction internally through the device. This represents the "on" position for the device. A 180° rotation of the collar from the "on" position represents the "off" position for the device. In the "off" position, the two holes are occluded and the device will work normally using the internal plunger.

In some embodiments, a removeable light-emitting diode (LED) or fiberoptic filament may provide light to aid in visualization. The light may attach to the body of the device itself, and may include an "on/off" button for control.

Embodiments of the tip are removable and disposable, and may have different sizes and diameters. The tip may also be constructed of a variety of materials that may include, by way of illustrative and nonlimiting example, a soft plastic, a soft foam, or a soft rubber or silicone. The tip itself may have a flared or straight tip, and inside the tip, it may contain a non-water-soluble adhesive material. This material could adhere to an FB when contact is made.

Further advantageously, the disposable tip may be manufactured such that a self-contained plunger or piston may be provided within the body of the tip itself.

In yet another embodiment, suction means are provided external to the mechanism itself. For example, an external harness may be provided as an attachment to a syringe, such as a 10 cc syringe. The harness includes a receiver that couples to the tip of the syringe, forming a pneumatic seal. The harness also includes a valve that occludes air flow between the tip of the attachment and the barrel of the syringe. In this case, the user can pull the piston of the syringe back, thus creating a vacuum or pseudo-vacuum within the chamber of the barrel. The user can then operate a trigger or other mechanism to open the valve, which then causes suction at the tip of the harness.

The foregoing can be used to build or embody several example implementations, according to the teachings of the present specification. Some example implementations are included here as nonlimiting illustrations of these teachings.

By way of example, there is disclosed an apparatus for extracting a foreign body (FB) from a bodily orifice, comprising: a connector having a receiver to pneumatically seal to a suction source; a hollow shaft pneumatically coupled to the connector; a hollow tip pneumatically coupled to the hollow shaft; and a valve disposed between the hollow tip and the connector, wherein the valve is disposed, when closed, to pneumatically isolate the hollow tip from the connector, and when open to allow a continuous air flow passage between the connector and the hollow tip; and means to open the valve.

There is further disclosed an example, wherein the hollow tip is flared.

There is further disclosed an example, wherein the hollow tip comprises an adhesive coating.

There is further disclosed an example, wherein the adhesive coating is a sticky adhesive.

There is further disclosed an example, wherein the adhesive coating is a tacky adhesive.

There is further disclosed an example, wherein the receiver comprises a smooth bore to couple to a smooth tip of the suction source.

There is further disclosed an example, wherein the receiver comprises a threaded bore to couple to a threaded tip of the suction source.

There is further disclosed an example, wherein the suction source is a syringe.

There is further disclosed an example, wherein the syringe is a 10 cubic centimeter syringe.

There is further disclosed an example, further comprising a piston stop to secure a piston of the syringe in a drawn back position.

There is further disclosed an example, wherein the piston stop has a linear dimension to secure the piston at a position to form, within a barrel of the syringe, a vacuum or pseudo-vacuum having a volume of approximately 10 cubic centimeters.

There is further disclosed an example, wherein the suction source is an oral syringe.

There is further disclosed an example, wherein the apparatus is a single piece construction.

There is further disclosed an example, wherein the apparatus is a multi-piece construction.

There is further disclosed an example, wherein the suction source includes an active suction source.

There is further disclosed an example, wherein the apparatus is disposable.

There is further disclosed an example of an extraction device for ear, nose, and throat (ENT) applications, comprising: a hollow barrel; a mechanical primer comprising a piston having an airtight fit within an inner circumference of the hollow barrel; wherein the piston sits proximate to a stop in a first position and removed from the stop in a second position, wherein a vacuum or pseudo-vacuum develops between the piston and the stop in the second position; a conduit pneumatically coupled to the hollow barrel, and separated from the hollow barrel by a valve, the valve when closed to maintain the vacuum; a tip on the conduit having a concave surface, the concave surface pneumatically coupled to the conduit; and a release trigger to open the valve, whereby air within the conduit is drawn into the vacuum to create a suction force at the concave surface.

There is further disclosed an example, wherein the valve is spring loaded, with the spring biased toward a closed position.

There is further disclosed an example, further comprising biasing means to bias the valve toward a closed position, wherein the release trigger is disposed to open the valve.

There is further disclosed an example, further comprising a port to pneumatically couple to a continuous suction source.

There is further disclosed an example, further comprising a rotatable collar around the hollow barrel, the rotatable collar to open the port in a first position and occlude the port in a second position.

There is further disclosed an example, further comprising securing means to secure a foreign body to the tip.

There is further disclosed an example, wherein the securing means comprise an adhesive.

There is further disclosed an example, wherein the securing means comprise a tacky glue.

There is further disclosed an example, wherein the conduit and tip have dimensions to fit in the nose of a human child.

There is further disclosed an example, wherein the conduit and tip have dimensions to fit in the nose of a human adult.

There is further disclosed an example, wherein the conduit and tip have dimensions to fit in a human ear.

There is further disclosed an example, wherein the conduit and tip comprise a disposable attachment to the hollow barrel.

There is further disclosed an example of a disposable extractor attachment for a syringe, comprising: a receiver to seal to a tip of the syringe;

a hollow shaft extending from the receiver, and terminating in a concave tip, the concave tip having thereon securing means to secure a foreign body (FB) to the concave tip; a valve disposed between the hollow shaft and the receiver, the valve biased to closed position; and a trigger to open the valve.

There is further disclosed an example, wherein the concave tip is flared.

There is further disclosed an example, wherein the concave tip comprises an adhesive coating.

There is further disclosed an example, wherein the adhesive coating is a sticky adhesive.

There is further disclosed an example, wherein the adhesive coating is a tacky adhesive.

There is further disclosed an example, wherein the receiver comprises a smooth bore to couple to a smooth tip of the syringe.

There is further disclosed an example, wherein the receiver comprises a threaded bore to couple to a threaded tip of the syringe.

There is further disclosed an example, wherein the syringe is a 10 cubic centimeter syringe.

There is further disclosed an example, wherein the syringe is between 2 cubic centimeters and 15 cubic centimeters.

There is further disclosed an example of a single piece harness comprising the disposable extractor attachment.

There is further disclosed an example, further comprising one or more clips to secure the single piece harness to the syringe.

There is further disclosed an example, further comprising a piston stop to secure a piston of the syringe in a drawn back position.

A system and method of providing a foreign body extractor for ears, nose, and throat will now be described with more particular reference to the attached FIGURES. It should be noted that throughout the FIGURES, certain reference numerals may be repeated to indicate that a particular device or block is referenced multiple times across several FIGURES. In other cases, similar elements may be given new numbers in different FIGURES. Neither of these practices is intended to require a particular relationship between the various embodiments disclosed. In certain examples, a genus or class of elements may be referred to by a reference numeral ("widget 10"), while individual species or examples of the element may be referred to by a hyphenated numeral ("first specific widget 10-1" and "second specific widget 10-2").

Figure 1B:
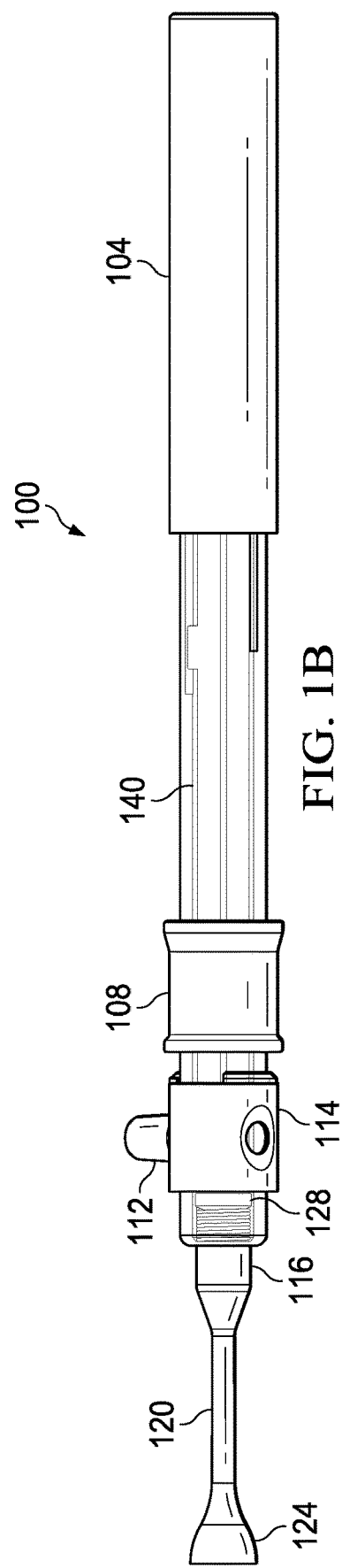

FIGS. 1A and 1B illustrate selected elements of a side view of an ENT extractor 100. In this illustration, extractor assembly 100 includes a barrel 104, having disposed therein a piston assembly 140. Piston assembly 140 may include, for example, a closure or gasket that creates an airtight seal within an inner diameter of barrel 104. Thus, when piston assembly 140 is in a fully downward position within barrel 104, there is little or no air within barrel 104.

Extractor assembly 100 also includes a grip 108, which may be, for example, a plastic or rubber grip. There is also a collar 114 having disposed therein a port 112.

A hollow shaft 120 is connected to barrel 104 via connector 116. Hollow shaft 120 may have a tip 124, which in this illustration is flared, and which may include a concave inner surface. Although a flared tip with a concave inner surface is illustrated, other tips may be used, such as a straight tip, or a tapered tip.

In the illustration of FIG. 1A, an inner spring within barrel 104 is in an uncompressed position, meaning that piston assembly 140 may be retracted, which may provide a transitory vacuum within at least a portion of barrel 104. In the illustration of FIG. 1B, piston assembly 140 is in a full downward position, and thus, the transitory vacuum is not developed.

Figure 2:
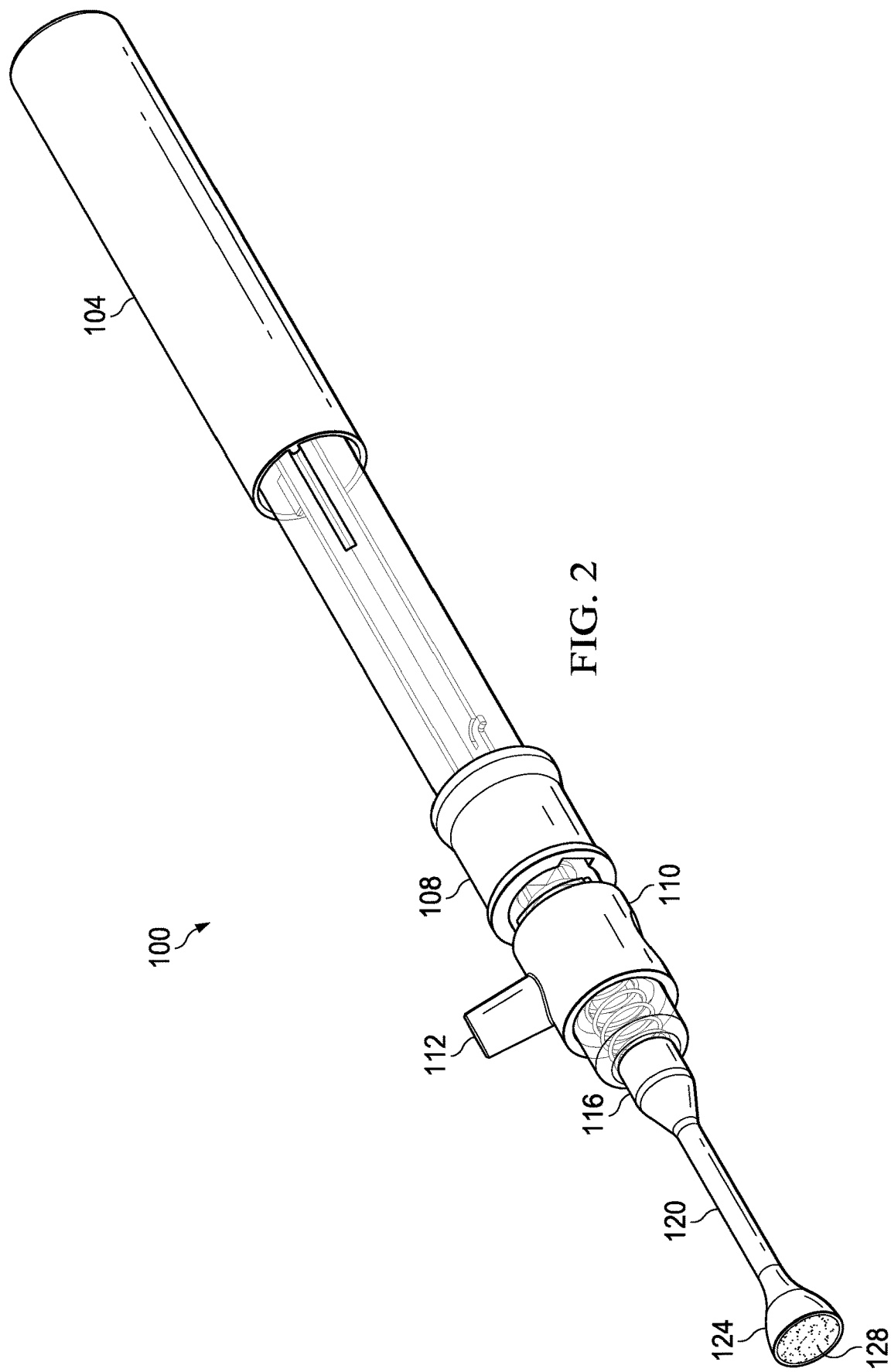
FIG. 2 is a perspective view of an ENT extractor assembly.

FIG. 2 is a perspective view of an ENT extractor assembly 100, further illustrating grip 108, rotatable collar 110, and port 112. Port 112 may be provided so that an active suction solution can be employed. For example, port 112 may be connected to a separate ENT mechanism that may be available for use in a physician's office. This ENT mechanism may develop continuous suction, and an appropriate connector such as a flexible tube or hose may be connected to port 112. Collar 110 is rotatable, so that in a first position, port 112 aligns with an inner port aperture within barrel 104. In a second position, port 112 is rotated away from the port aperture of barrel 104, and the port aperture is occluded, thus occluding the port mechanism. Thus, when it is desirable to use the port, collar 110 may be rotated into position so that the port aperture is unoccluded, and the continuous suction solution can be deployed with a tube or hose connected to port 112. When the active suction solution is not to be used, then rotatable collar 110 may be rotated to the second position, wherein the port is occluded, and the port aperture is pneumatically sealed by collar 110.

Also visible in this view, tip 124 may have disposed thereon an adhesive coating 128. Adhesive 128 may be a glue, a tacky glue, or some other tacky or sticky substance. In more general terms, any appropriate securing means may be provided within tip 124, so that when an FB is drawn toward tip 124, once contact is made, the securing means will secure the FB to tip 124.

FIGS. 3A and 3B are a cutaway side view of an ENT extractor assembly 100 illustrating example internal mechanisms. In general, barrel 104 may provide some suction means or vacuum means to provide a suction force within hollow shaft 120, and at the end of tip 124. Thus, in operational use, an ENT professional, other medical provider, or a home user may insert tip 124 into an orifice, such as an ear or a nose that has become obstructed by an FB. The user may then operate the barrel 104 to develop a suction at tip 124, which will draw the FB toward tip 124. Securing means on tip 124, such as an adhesive or tacky substance, then secures the FB to tip 124. Once the FB is secured to tip 124, the ENT professional or home user may extract the FB from the orifice.

FIGS. 3A and 3B illustrate one illustrative means of developing the suction force.

In this example, a plunger 144 sits at the end of a piston assembly 308. Plunger 144 may pneumatically seal to an inner diameter of barrel 104. In this example, piston assembly 308 includes two operational springs, namely spring 304, and recoil spring 316. A user may grip barrel 104 at outer diameter 312, and then operate trigger 113, which is mechanically coupled to spring 304. When trigger 113 is operated, spring 304 is released from a compressed position (as illustrated in FIG. 3B), and extended to an extended position (as illustrated in FIG. 3A). When spring 304 decompresses, recoil spring 316 (which may have a lighter spring constant than spring 304) helps to absorb some of the recoil shock. When plunger 144 retreats from a position proximate to shaft 120, it develops a suction force within shaft 120, and at tip 124.

Figure 5:
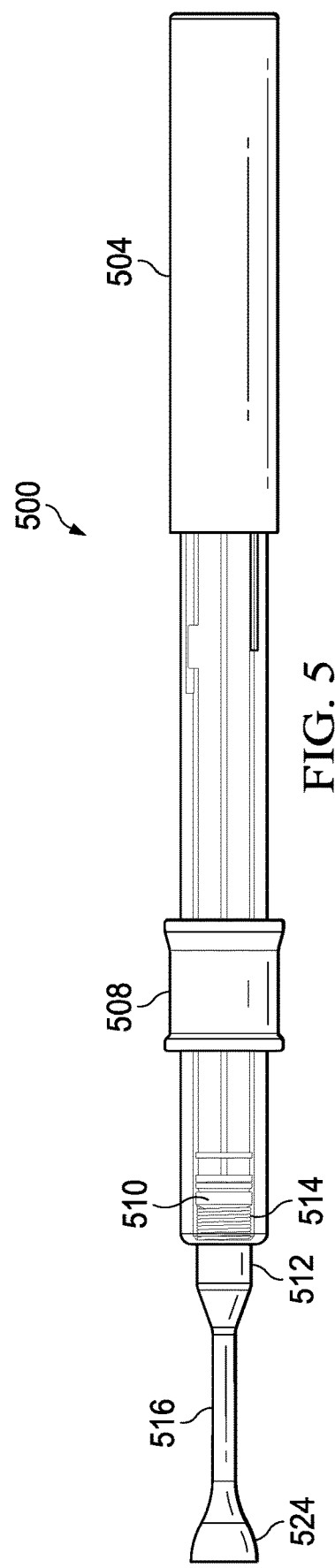
FIG. 5 is a side view illustration of another embodiment of an ENT extractor.
Figure 6:
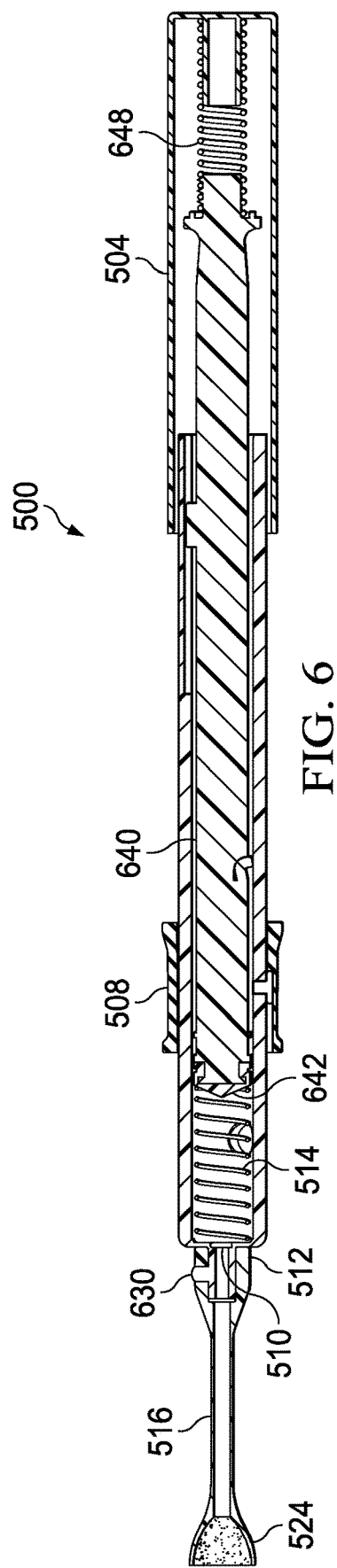
FIG. 6 illustrates a recoil spring in a compressed state, and a piston assembly in a retracted position.

The embodiment illustrated in FIGS. 3A and 3B develops a suction force without the need to prime a vacuum. While this is simpler in operation, in some embodiments, the suction force developed is less than the suction force developed in a case where the vacuum is primed. Thus, in other embodiments, the vacuum may be primed. For example, FIGS. 5 and 6 illustrate an embodiment wherein a vacuum may be primed before it is released, which may develop greater suction than the present embodiment. The trade-off between simplicity of operation and the desire to create a greater suction force is a design consideration that may depend on the specific embodiment and its application.

Furthermore, in this or in other embodiments where active suction is to be used, the collar may be rotated to open a port aperture, to provide for active suction. In that case, the transitory vacuum or suction force created by the spring mechanism may be unnecessary, and may be bypassed.

Figure 4:
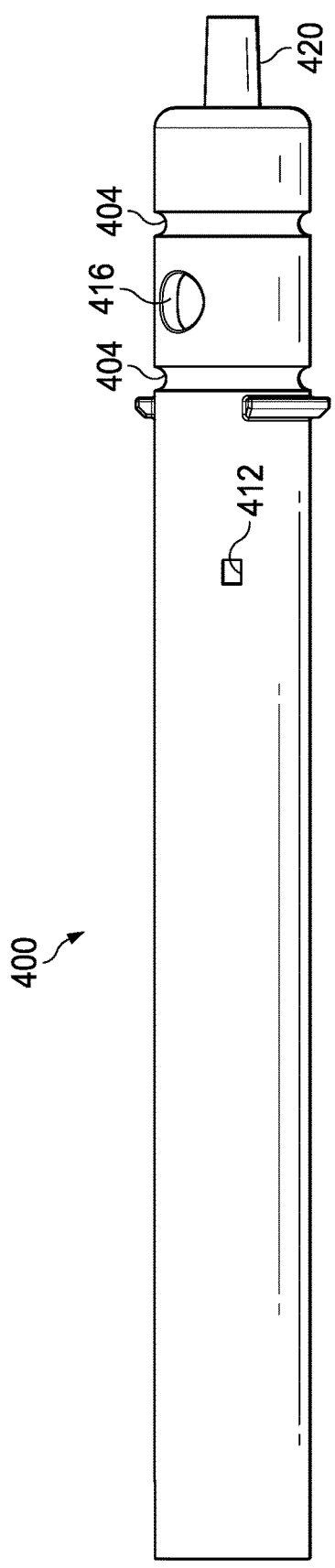
FIG. 4 is a side view illustrating selected aspects of a barrel.

FIG. 4 is a side view illustrating selected aspects of a barrel 400. In this example, barrel 400 includes a trigger aperture 412, which has an aperture to receive a trigger, such as trigger 113 of FIG. 1A.

Also shown in this example is port aperture 416, which when aligned with a port such as port 112 of FIG. 1, is open to provide active suction to the device. On either side of port aperture 416 are tracks 404, which may enable a collar such as collar 114 of FIG. 1A to rotate around and seal to port aperture 416.

Barrel 400 also includes a tip receiver 420, which may securely pneumatically couple to a disposable shaft assembly, which may include shaft 120 with connector 116 and tip 124, as illustrated in FIG. 1A.

FIG. 5 is a side view illustration of another embodiment of an ENT extractor 500. In this example, ENT extractor 500 includes a barrel assembly 504. Barrel assembly 504 may be used to draw back a piston assembly 640, as illustrated in FIG. 6. Barrel assembly 504 is one embodiment; however, grip 508 could also operate the piston assembly.

In this embodiment, barrel assembly 504 is similar to a syringe, such as an oral syringe. As before, a shaft 516 has a tip 524 that is to draw an FB to tip 524 when a suction force is developed at tip 524. Shaft 516 and tip 524 connect to sliding handle 504 at connector 512.

Barrel assembly 504 is different from the barrel illustrated in FIG. 1, because it requires priming of a vacuum or pseudo-vacuum to develop the suction force. This can be more readily seen in FIG. 6.

FIG. 6 illustrates a recoil spring 514 in a compressed state, and a piston assembly 640 in a retracted position. Plunger 642 is withdrawn from valve 510, thus creating a vacuum or pseudo-vacuum in the space between plunger 642 and valve 510. In this case, spring 648 may be the stiffer spring, while recoil spring 514 may have a lower spring constant. When a user draws back piston assembly 640, spring 648 is compressed. The user may then operate trigger 630 to open valve 510, which may be spring-loaded, or have other biasing means to bias the valve closed. When the biasing means are released, valve 510 opens, and the vacuum or pseudo-vacuum within barrel 504 creates suction pressure within shaft 516 at tip 524.

Note that the term pseudo-vacuum is used herein to describe a near-vacuum or a vacuum-like condition. A pseudo-vacuum may occur when piston assembly 640 is moved upward, thus creating a lower pressure zone within barrel 504. Although this may not be a true vacuum, the pressure differential between the pseudo-vacuum and the ambient environment creates the necessary conditions for the suction force within shaft 516 and at tip 524.

Figure 7:
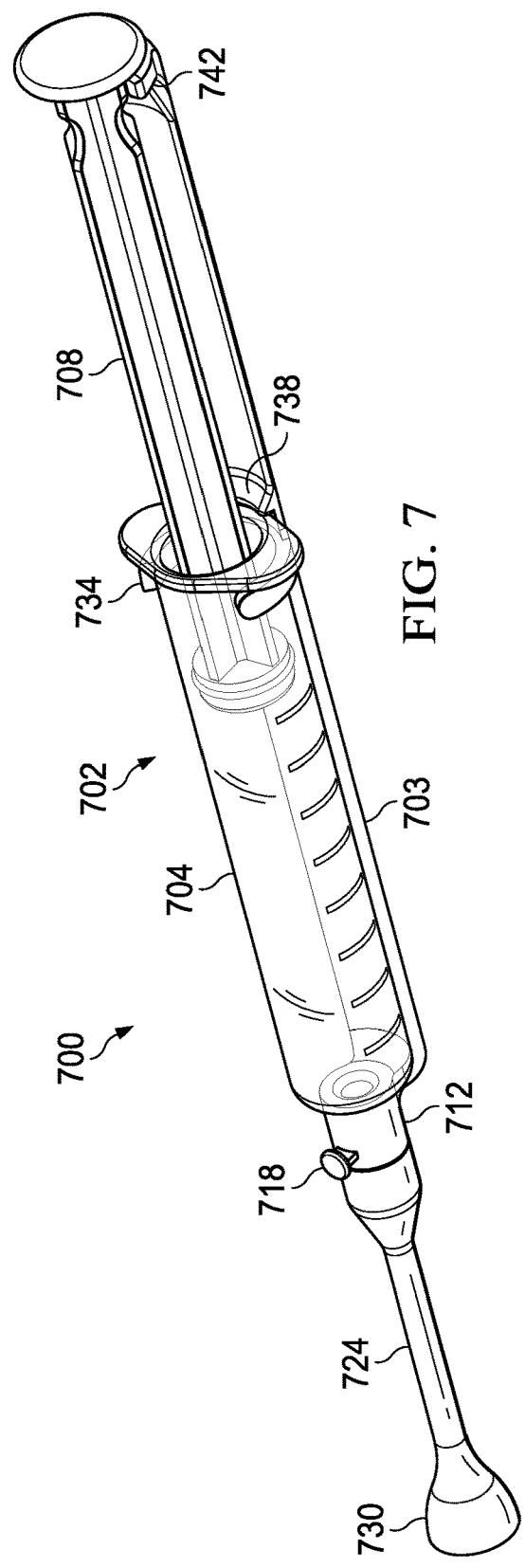
FIG. 7 illustrates a perspective view of an illustrative embodiment of a hybrid assembly.
Figure 8:
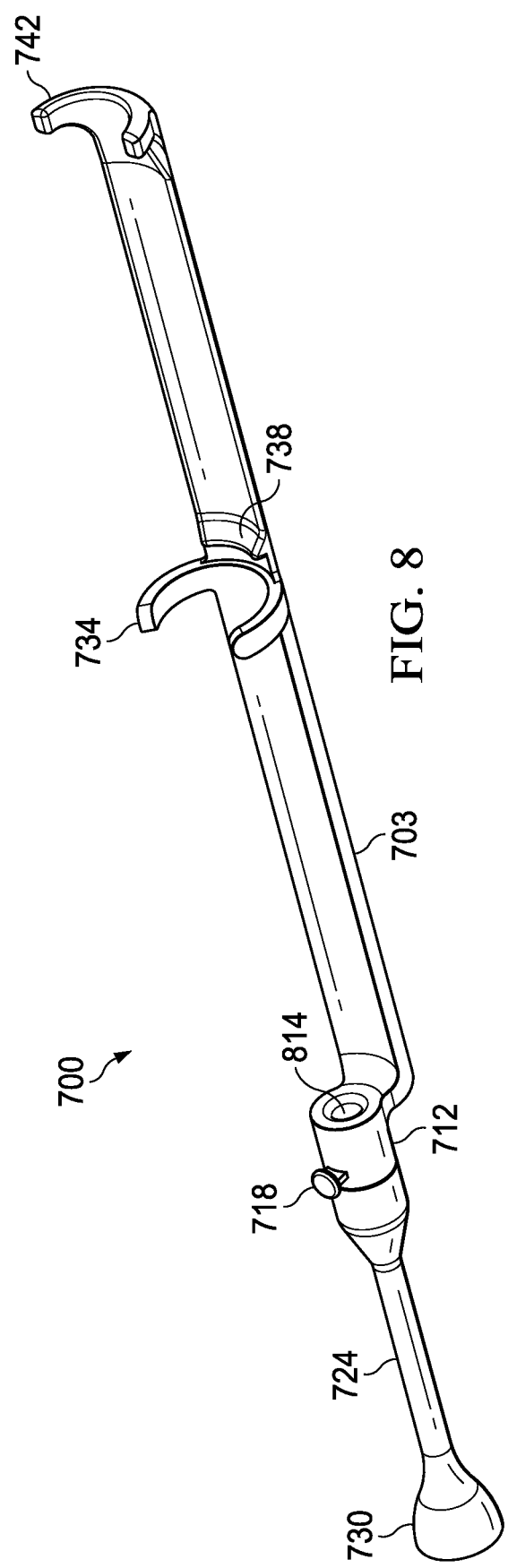
FIG. 8 illustrates is a perspective view of an embodiment of a disposable attachment harness.

FIG. 7 illustrates a perspective view of an illustrative embodiment of a hybrid assembly 700. FIG. 8 provides a perspective view of a disposable harness assembly, separate from a syringe. Hybrid assembly 700 includes a disposable harness 703, which may be attached to a disposable or non-disposable parent part, such as a syringe 702. In this example, syringe 702 may be a 10 mm syringe, such as a syringe designed to receive a hypodermic needle, or a 10 mL oral syringe. Note that in some cases, a 10 mL syringe could also be a 10 cc syringe. Other syringe sizes could be used, such as a 2 cc syringe, a 3 cc syringe, a 5 cc syringe, or a 15 cc syringe, by way of illustrative and nonlimiting example.

One advantage of using an existing syringe is that syringes can be acquired off-the-shelf, and are widely available. Indeed, many medical facilities and doctors' offices will already have a wide variety of syringes readily available. Syringe 702 already includes means to develop a vacuum, namely a piston 708 and barrel 704, with piston 708 fitting securely within an inner diameter of barrel 704. Air can pass through a tip of syringe 702, which is not seen in this view because the tip has been obscured by harness 703.

Harness 703 may include one or more parts that can be attached to syringe 702. For example, harness 703 may have a structural body to connect a piston stop 742 to a tip attachment, including shaft 724 and tip 730.

Shaft 724 may include a valve 712 disposed within shaft 724, and disposed to block the tip of syringe 702. When valve 712 is closed, then a vacuum can be developed by pulling back on piston 708. In some embodiments, valve 712 defaults to a closed position. When valve button 718 is pressed, valve 712 opens, and a vacuum or pseudo-vacuum within barrel 704 may cause suction at tip 730.

For convenience, harness 703 may be provided as a single piece, although multi-piece construction is also anticipated. In addition to the shaft assembly, harness 703 includes a piston stop 742. When a user pulls back on piston 708 with valve 712 closed, a vacuum or pseudo-vacuum develops within barrel 704. This vacuum or pseudo-vacuum will tend to pull piston 708 back down, to resist the vacuum. Thus, it is desirable to have a piston stop 742, which can hold piston 708 in its pulled back or retracted position. In this case, harness 703 includes a wing clip 738, which clips over a wing 734 of syringe 702. Wing 734 may be designed so that human fingers, such as an index finger and middle finger, can wrap around barrel 704, while a user uses a thumb to press piston 708. Wing 734 also can provide a convenient mount for harness 703, and because wing clip 738 engages wing 734 at both the top and bottom, it provides a secure fit. Piston stop 742 also clips to the top of piston 708.

Thus, a user can secure harness 703 to syringe 702, such as by sliding receiver 814 (FIG. 8) of harness 703 over the tip of syringe 702 (in the case of a smooth tip on syringe 702), or by screwing the tip into receiver 814 of harness 703 (e.g., in the case of a threaded tip). Once the tip of syringe 702 is secured to receiver 814 of harness 703, wing clip 738 may be snapped or clipped to wing 734. The user can then pull back on piston 708 until it is fully withdrawn, or withdrawn to a desired extent. Once piston 708 is drawn back, the user can clip piston stop 742 to the top of piston 708, which secures piston 708 in its position. Thus, the vacuum or pseudo-vacuum within barrel 704 is maintained, until the user presses valve button 718. When the user presses valve button 718, a spring, or other mechanical release, releases valve 712, thus allowing airflow from tip 730 through shaft 724 and into barrel 704. This airflow provides suction at tip 730, which suction may help to secure the foreign object to tip 730. Harness 703 may be mounted to syringe 702 by the user, who then pulls back piston 708 and secures it with piston stop 742. This develops a vacuum or pseudo-vacuum within barrel 704.

Throughout this specification, several valves are disclosed, which valves may be configured to maintain a pneumatic seal between the shaft or conduit and the suction source (when closed), and then provide an open-air pathway between the shaft and suction source when open. Many types of valves are known in the art, and any suitable valve may be used with the embodiments shown in any of FIGS. 1-8 above. For example, a reed valve or other one-way valve may be used to allow air to flow from the suction source to the conduit. This may be useful in cases where it may be necessary to expel air, such as to reset the apparatus for a "second try" (if a first extraction fails), or where a trigger is accidentally operated.

In any of these examples, the valve may include biasing means, which biases the valve to either an open or a closed position. The choice of whether to bias the valve open or closed is a design choice. In cases where the valve is biased open, securing means (such as a tab or stopper) may be in place to hold the valve closed until the trigger is operated to release the valve. If the valve is biased closed, then the trigger may open the valve for only so long as the trigger is active depressed or operated. Thus, once the trigger is released, the valve closes again. In these cases, the biasing means (such as a spring) may need to be strong enough to hold the valve closed once the vacuum is developed. Alternatively, the valve could be biased closed, and in addition a tab, stopper, or other securing means could be provided to further secure the valve at its closed position. In those cases, the trigger may be configured to both release the securing means and move the valve to an open position.

The teachings of the present specification provide an inexpensive and safety-enhanced method for removing foreign bodies from ears, nose, or throat. One particular challenge in using an extractor is that if the practitioner presses too hard against the FB with the extractor, the practitioner may simply drive the FB further into the orifice. Thus, in an illustrative use case, the user, such as a physician or nurse, inserts tip 730 and shaft 724 into the orifice, until it gently touches or nearly touches the FB. Once tip 730 gently touches or nearly touches the FB, the user presses valve button 718. This opens the valve, and provides suction at tip 730. The suction may then be sufficient to pull the FB toward tip 730, which as described above may have an adhesive end, or other gripping means. The gripping means then secure the FB to tip 730, and the user or practitioner can safely remove the FB from the orifice.

The foregoing outlines features of several embodiments so that those skilled in the art may better understand various aspects of the present disclosure. The embodiments disclosed can readily be used as the basis for designing or modifying other processes and structures to carry out the teachings of the present specification. Any equivalent constructions to those disclosed do not depart from the spirit and scope of the present disclosure. Design considerations may result in substitute arrangements, design choices, device possibilities, hardware configurations, software implementations, and equipment options.

There are also provided herein certain methods, illustrated for example in flow charts and/or signal flow diagrams. The order or operations disclosed in these methods discloses one illustrative ordering that may be used in some embodiments, but this ordering is no intended to be restrictive, unless expressly stated otherwise. In other embodiments, the operations may be carried out in other logical orders. In general, one operation should be deemed to necessarily precede another only if the first operation provides a result required for the second operation to execute. Furthermore, the sequence of operations itself should be understood to be a nonlimiting example. In appropriate embodiments, some operations may be omitted as unnecessary or undesirable. In the same or in different embodiments, other operations not shown may be included in the method to provide additional results.

In certain embodiments, some of the components illustrated herein may be omitted or consolidated. In a general sense, the arrangements depicted in the FIGURES may be more logical in their representations, whereas a physical architecture may include various permutations, combinations, and/or hybrids of these elements.

With the numerous examples provided herein, interaction may be described in terms of two, three, four, or more electrical or mechanical components. These descriptions are provided for purposes of clarity and example only. Any of the illustrated components, modules, and elements of the FIGURES may be combined in various configurations, all of which fall within the scope of this specification.

In certain cases, it may be easier to describe one or more functionalities by disclosing only selected element. Such elements are selected to illustrate specific information to facilitate the description. The inclusion of an element in the FIGURES is not intended to imply that the element must appear in the disclosure, as claimed, and the exclusion of certain elements from the FIGURES is not intended to imply that the element is to be excluded from the disclosure as claimed. Similarly, any methods or flows illustrated herein are provided by way of illustration only. Inclusion or exclusion of operations in such methods or flows should be understood the same as inclusion or exclusion of other elements as described in this paragraph. Where operations are illustrated in a particular order, the order is a nonlimiting example only. Unless expressly specified, the order of operations may be altered to suit a particular embodiment.

Other changes, substitutions, variations, alterations, and modifications will be apparent to those skilled in the art. All such changes, substitutions, variations, alterations, and modifications fall within the scope of this specification.

In order to aid the United States Patent and Trademark Office (USPTO) and, any readers of any patent or publication flowing from this specification, the Applicant: (a) does not intend any of the appended claims to invoke paragraph (f) of 35 U.S.C. section 112, or its equivalent, as it exists on the date of the filing hereof unless the words "means for" or "steps for" are specifically used in the particular claims; and (b) does not intend, by any statement in the specification, to limit this disclosure in any way that is not otherwise expressly reflected in the appended claims, as originally presented or as amended.

What is claimed is:

1. An apparatus for extracting a foreign body (FB) from a bodily orifice, comprising:
   a connector having a receiver to pneumatically seal to a suction source;
   a hollow shaft pneumatically coupled to the connector;
   a hollow tip pneumatically coupled to the hollow shaft; and
   a valve disposed between the hollow tip and the connector, wherein the valve is disposed, when closed, to pneumatically isolate the hollow tip from the connector, and when open to allow a continuous air flow passage between the connector and the hollow tip; and
   means to open the valve.

2. The apparatus of claim 1, wherein the hollow tip is flared.

3. The apparatus of claim 1, wherein the hollow tip comprises an adhesive coating.

4. The apparatus of claim 3, wherein the adhesive coating is a sticky adhesive.

5. The apparatus of claim 3, wherein the adhesive coating is a tacky adhesive.

6. The apparatus of claim 1, wherein the receiver comprises a smooth bore to couple to a smooth tip of the suction source.

7. The apparatus of claim 1, wherein the receiver comprises a threaded bore to couple to a threaded tip of the suction source.

8. The apparatus of claim 1, wherein the suction source is a syringe.

9. The apparatus of claim 8, wherein the syringe is a 10 cubic centimeter syringe.

10. The apparatus of claim 8, further comprising a piston stop to secure a piston of the syringe in a drawn back position.

11. The apparatus of claim 10, wherein the piston stop has a linear dimension to secure the piston at a position to form, within a barrel of the syringe, a vacuum or pseudo-vacuum having a volume of approximately 10 cubic centimeters.

12. The apparatus of claim 1, wherein the suction source is an oral syringe.

13. The apparatus of claim 1, wherein the apparatus is a single piece construction.

14. The apparatus of claim 1, wherein the apparatus is a multi-piece construction.

15. The apparatus of claim 1, wherein the suction source includes an active suction source.

16. The apparatus of claim 1, wherein the apparatus is disposable.

17. An extraction device for ear, nose, and throat (ENT) applications, comprising:
   a hollow barrel;
   a mechanical primer comprising
   a piston having an airtight fit within an inner circumference of the hollow barrel; wherein the piston sits proximate to a stop in a first position and removed from the stop in a second position, wherein a vacuum or pseudo-vacuum develops between the piston and the stop in the second position;
   a conduit pneumatically coupled to the hollow barrel, and separated from the hollow barrel by a valve, the valve when closed to maintain the vacuum;
   a tip on the conduit having a concave surface, the concave surface pneumatically coupled to the conduit; and
   a release trigger to open the valve, whereby air within the conduit is drawn into the vacuum to create a suction force at the concave surface.

18. The extraction device of claim 17, wherein the valve is spring loaded, with the spring biased toward a closed position.

19. The extraction device of claim 17, further comprising biasing means to bias the valve toward a closed position, wherein the release trigger is disposed to open the valve.

20. The extraction device of claim 17, further comprising a port to pneumatically couple to a continuous suction source.

21. The extraction device of claim 20, further comprising a rotatable collar around the hollow barrel, the rotatable collar to open the port in a first position and occlude the port in a second position.

22. The extraction device of claim 17, further comprising securing means to secure a foreign body to the tip.

23. The extraction device of claim 22, wherein the securing means comprise an adhesive.

24. The extraction device of claim 22, wherein the securing means comprise a tacky glue.

25. The extraction device of claim 17, wherein the conduit and tip have dimensions to fit in the nose of a human child.

26. The extraction device of claim 17, wherein the conduit and tip have dimensions to fit in the nose of a human adult.

27. The extraction device of claim 17, wherein the conduit and tip have dimensions to fit in a human ear.

28. The extraction device of claim 17, wherein the conduit and tip comprise a disposable attachment to the hollow barrel.

29. A disposable extractor attachment for a syringe, comprising:
   a receiver to seal to a tip of the syringe;
   a hollow shaft extending from the receiver, and terminating in a concave tip, the concave tip having thereon securing means to secure a foreign body (FB) to the concave tip;
   a valve disposed between the hollow shaft and the receiver, the valve biased to closed position; and
   a trigger to open the valve.

30. The disposable extractor attachment of claim 29, wherein the concave tip is flared.

31. The disposable extractor attachment of claim 29, wherein the concave tip comprises an adhesive coating.

32. The disposable extractor attachment of claim 31, wherein the adhesive coating is a sticky adhesive.

33. The disposable extractor attachment of claim 31, wherein the adhesive coating is a tacky adhesive.

34. The disposable extractor attachment of claim 29, wherein the receiver comprises a smooth bore to couple to a smooth tip of the syringe.

35. The disposable extractor attachment of claim 29, wherein the receiver comprises a threaded bore to couple to a threaded tip of the syringe.

36. The disposable extractor attachment of claim 29, wherein the syringe is a 10 cubic centimeter syringe.

37. The disposable extractor attachment of claim 29, wherein the syringe is between 2 cubic centimeters and 15 cubic centimeters.

38. A single piece harness comprising the disposable extractor attachment of claim 29.

39. The single piece harness of claim 38, further comprising one or more clips to secure the single piece harness to the syringe.

40. The single piece harness of claim 38, further comprising a piston stop to secure a piston of the syringe in a drawn back position.

* * * * *